United States Patent
Shelton, IV et al.

(10) Patent No.: US 10,849,698 B2
(45) Date of Patent: Dec. 1, 2020

(54) ROBOTICS TOOL BAILOUTS

(71) Applicant: Ethicon Endo-Surgery, LLC, Guaynabo, PR (US)

(72) Inventors: Frederick E. Shelton, IV, Hillsboro, OH (US); Jason L. Harris, Lebanon, OH (US)

(73) Assignee: Ethicon LLC, Guaynabo, PR (US)

( * ) Notice: Subject to any disclaimer, the term of this patent is extended or adjusted under 35 U.S.C. 154(b) by 875 days.

(21) Appl. No.: 15/238,219

(22) Filed: Aug. 16, 2016

(65) Prior Publication Data
US 2018/0051780 A1 Feb. 22, 2018

(51) Int. Cl.
*A61B 34/30* (2016.01)
*A61B 34/00* (2016.01)
*A61B 90/00* (2016.01)

(52) U.S. Cl.
CPC ............. *A61B 34/30* (2016.02); *A61B 34/71* (2016.02); *A61B 2034/305* (2016.02); *A61B 2034/715* (2016.02); *A61B 2090/031* (2016.02)

(58) Field of Classification Search
CPC ... A61B 90/03; A61B 2090/031; A61B 34/30; A61B 34/70; A61B 34/71; A61B 2034/715
See application file for complete search history.

(56) References Cited

U.S. PATENT DOCUMENTS

| | | | |
|---|---|---|---|
| 8,114,345 B2 | 2/2012 | Dlugos, Jr. et al. | |
| 8,882,792 B2 | 11/2014 | Dietz et al. | |
| 8,915,842 B2 | 12/2014 | Weisenburgh, II et al. | |
| 8,931,682 B2 | 1/2015 | Timm et al. | |
| 8,945,098 B2 | 2/2015 | Seibold et al. | |
| 2008/0081948 A1 | 4/2008 | Weisenburgh et al. | |
| 2008/0237298 A1* | 10/2008 | Schall | A61B 17/07207 227/180.1 |

(Continued)

OTHER PUBLICATIONS

Correlated Solutions, "Principle of Digital Image Correlation," 2013 (http://correlatedsolutions.com/digital-image-correlation/).

(Continued)

*Primary Examiner* — Diane D Yabut
*Assistant Examiner* — Majid Jamialahmadi
(74) *Attorney, Agent, or Firm* — Mintz Levin Cohn Ferris Glovsky and Popeo, P.C.

(57) ABSTRACT

Various surgical tools with bailout mechanisms are provided that allow direct engagement with one or more actuators to provide rapid and effective bailout (such as release, reversal, and/or retraction) of surgical tools while minimizing the amount of force and/or time to complete the bailout. Robotic surgical tools generally have a housing and an elongate tool shaft extending from the housing and having an end effector on a distal end thereof. The housing has a plurality of actuators for causing various functions of the end effector, such as rotation, articulation, clamping, firing, stapling, etc. The housing attaches to a tool driver on a robotic arm that electromechanically drives the actuators to control the end effector. A bailout mechanism can extend from the housing into the elongate shaft and directly engage the actuators to apply a force thereto to retract an actuator.

14 Claims, 10 Drawing Sheets

(56) References Cited

U.S. PATENT DOCUMENTS

| | | | |
|---|---|---|---|
| 2010/0089970 A1* | 4/2010 | Smith | A61B 17/07207 |
| | | | 227/175.1 |
| 2011/0118709 A1 | 5/2011 | Burbank | |
| 2011/0118778 A1 | 5/2011 | Burbank | |
| 2013/0282052 A1 | 10/2013 | Aranyi et al. | |
| 2014/0005718 A1 | 1/2014 | Shelton, IV et al. | |
| 2015/0025571 A1* | 1/2015 | Suzuki | A61B 17/2909 |
| | | | 606/205 |
| 2018/0153629 A1* | 6/2018 | Wallace | A61B 34/30 |

OTHER PUBLICATIONS

U.S. Appl. No. 15/131,963 entitled "Method for Operating a Surgical Instrument" filed on Apr. 18, 2016.

U.S. Appl. No. 15/177,430 entitled "Surgical Instrument With User Adaptable Techniques" filed on Jun. 9, 2016.

* cited by examiner

ROBOTICS TOOL BAILOUTS

FIELD OF THE INVENTION

Methods and devices are provided for robotic surgery, and in particular for retracting and/or bailing out robotic tools.

BACKGROUND OF THE INVENTION

Minimally invasive surgical (MIS) instruments are often preferred over traditional open surgical devices due to the reduced post-operative recovery time and minimal scarring. Laparoscopic surgery is one type of MIS procedure in which one or more small incisions are formed in the abdomen and a trocar is inserted through the incision to form a pathway that provides access to the abdominal cavity. The trocar is used to introduce various instruments and tools into the abdominal cavity, as well as to provide insufflation to elevate the abdominal wall above the organs. The instruments and tools can be used to engage and/or treat tissue in a number of ways to achieve a diagnostic or therapeutic effect. Endoscopic surgery is another type of MIS procedure in which elongate flexible shafts are introduced into the body through a natural orifice.

Although traditional minimally invasive surgical instruments and techniques have proven highly effective, newer systems may provide even further advantages. For example, traditional minimally invasive surgical instruments often deny the surgeon the flexibility of tool placement found in open surgery. Difficulty is experienced in approaching the surgical site with the instruments through the small incisions. Additionally, the added length of typical endoscopic instruments often reduces the surgeon's ability to feel forces exerted by tissues and organs on the end effector. Furthermore, the relative remoteness of the instruments makes responding to any emergencies and/or errors during the surgery difficult. For example, if one or more instruments malfunction, it can be desirable to rapidly release any tissue coupled to the instruments and retract the instruments. But the remote placement of the instruments and the minimally-invasive nature of the surgery may make this desire difficult.

Thus it can be desirable to allow rapid release, reversal, and/or retraction of surgical instruments within a patient even if the instruments experience errors, malfunctions, and/or failures. While significant advances have been made in the field of robotic surgery, there remains a need for improved methods, systems, and devices for use in robotic surgery.

SUMMARY OF THE INVENTION

Various methods and devices are provided that include a bailout mechanism for retracting an actuator on a surgical tool when a failure is encountered. The methods and devices are particularly useful in connection with electrosurgical tools used with surgical robots, as the methods and devices are effective to disengage the actuator from the drive assembly and they allow direct retraction of the actuator.

In one embodiment, a surgical tool is provided and includes a housing configured to couple to a plurality of motors on a tool driver of a surgical robot. An elongate shaft extends distally from the housing and has an end effector coupled to a distal end thereof. A drive assembly is disposed within the housing and is configured to be driven by a motor on a tool driver of a surgical robot. An actuator extends through the elongate shaft and is operatively coupled between the drive assembly and the end effector for actuating the end effector. The device also includes a bailout mechanism directly coupled to the actuator and configured to apply a proximal force to the actuator to retract the actuator.

The tool can have a variety of configurations. In an exemplary embodiment, the bailout mechanism is configured to disengage the actuator from the drive assembly. For example, the bailout mechanism can include a bailout plate that is coupled to a proximal end of the actuator and that is configured to disengage the actuator from the drive assembly when the bailout plate is pulled proximally by the bailout mechanism to retract the actuator. The bailout mechanism can include a cable having a terminal end mated to a proximal end of the actuator. The bailout mechanism can also include a rotatable wheel disposed within the housing and configured to be rotated to apply a proximal force to the actuator. A crank arm can be provided for manually rotating the rotatable wheel. The assembly can also include a pawl coupled to the crank arm and engageable with the rotatable wheel. The pawl can be configured to rotate the wheel in a direction that causes retraction of the actuator. The tool can also include a pawl engaged with the rotatable wheel and configured to limit rotation of the rotatable wheel in only one direction.

In another embodiment, the actuator can be a first actuator and the bailout mechanism can be a first bailout mechanism. The device can include a second bailout mechanism extending from the housing into the elongate shaft. The second bailout mechanism can be directly coupled to a second actuator extending through the elongate shaft and operatively coupled between the drive assembly and the end effector for actuating the end effector. The second bailout mechanism can be configured to apply a proximal force thereto to the second actuator to retract the actuator. In certain exemplary embodiments, the actuator can be an articulation cable extending through the elongate shaft and configured to articulate the end effector.

In another embodiment, a surgical tool is provided and includes an elongate shaft, and an end effector coupled to a distal end of the elongate shaft. The end effector can include first and second jaws movable between an open position in which the first and second jaws are spaced apart from one another, and a closed position in which the first and second jaws are configured to engage tissue therebetween. A plurality of actuation members can extend distally through the elongate shaft for operating on the end effector. A plurality of driving members can each be coupled to a corresponding actuation member. Each driving member can be configured to actuate the corresponding actuation member. The plurality of actuation members can have a first configuration in which the plurality of actuation members are engaged with the corresponding drive members, and a second configuration in which the plurality of actuation members are disengaged from the corresponding drive members and are configured to be retracted proximally.

The surgical tool in certain aspects can include at least one bailout mechanism coupled to at least one of the plurality of actuation members. The at least one bailout mechanism can be configured to move the at least one of the plurality of actuation members from the first position to the second position. In other aspects, the device can include at least one crank arm coupled to at least one of the plurality of actuation members. The at least one crank arm can be configured to move the at least one actuation member from the first configuration to the second configuration and to proximally retract the at least one actuation member. In yet another embodiment, the device can include at least one pawl coupled to the at least one crank arm. The at least one pawl can be engageable with at least one gear coupled to a corresponding actuation member, and the at least one pawl can be configured to allow rotation of the at least one gear in only one direction when the at least one pawl is engaged with the gear.

In other aspects, a first pawl can be coupled to each of the at least one crank arms and engageable with a gear coupled to the actuation member, and a second pawl can be coupled to a housing of the surgical tool and engageable with the gear. The second pawl can be configured to slide longitudinally along the housing. The device can include other features such as an indicator disposed on the elongate shaft and configured to indicate if there is a failure in at least one of the plurality of actuation members. In other aspects, the plurality of driving members are disposed within a housing and are configured to couple to a plurality of motors on a tool driver of a surgical system.

Surgical methods are provided and in one embodiment a method includes activating at least one motor on a surgical robot to drive a driver disposed within a tool housing of a tool coupled to the surgical robot, the driver advancing an actuator through an elongate shaft of the tool to actuate an end effector coupled to a distal end of the elongate shaft. The method can also include manually actuating at least one bailout lever on the tool to disengage the actuator from the driver and to apply a force directly to the actuator to proximally retract the actuator. Actuating the at least one lever can include pivoting a crank arm coupled to the actuator until the actuator disengages from the driver and is proximally retracted.

BRIEF DESCRIPTION OF THE DRAWINGS

The invention will be more fully understood from the following detailed description taken in conjunction with the accompanying drawings, in which.

DETAILED DESCRIPTION OF THE INVENTION

Figure 1:
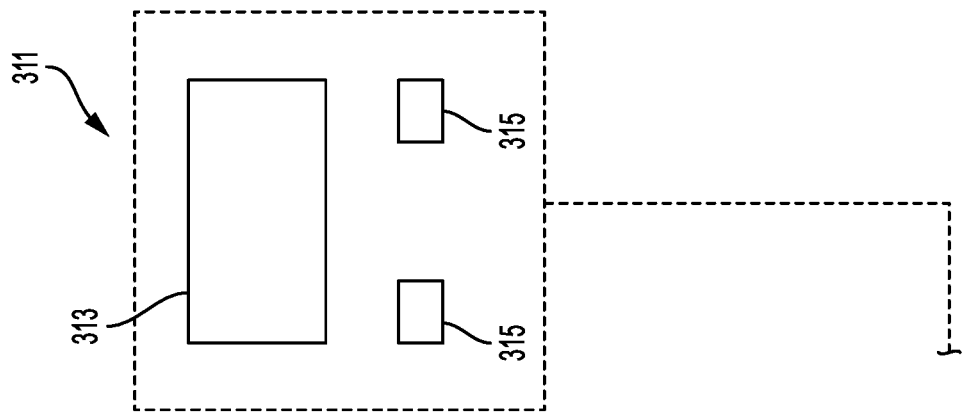
FIG. 1 is a perspective view of one embodiment of a surgical robotic system having one or more features consistent with the present description.
Figure 1:
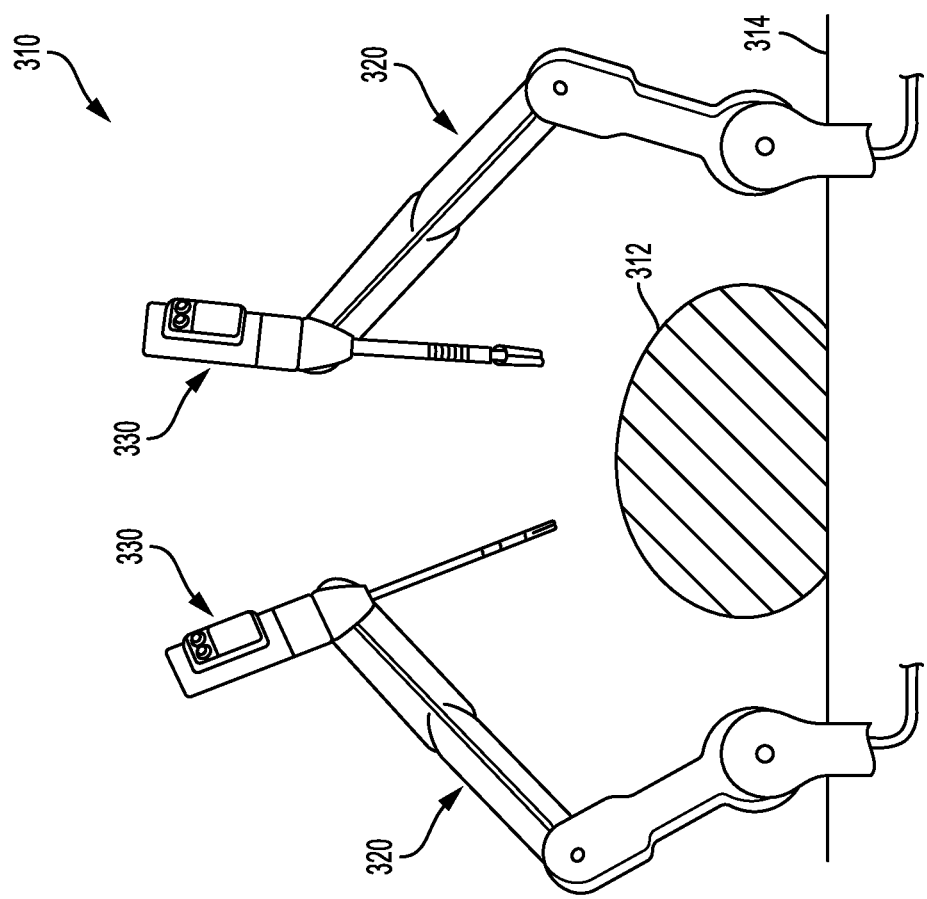

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

Various surgical tools with bailout mechanisms are provided. Robotic surgical tools generally have a housing and an elongate tool shaft extending from the housing and having an end effector on a distal end thereof. The housing has a plurality of drivers that are coupled to actuators extending through the tool shaft for causing various functions of the end effector, such as rotation, articulation, clamping, firing, stapling, etc. The housing attaches to a tool driver on a robotic arm that electromechanically drives the drivers and thereby the actuators to control the end effector.

Many surgical tools have various bailout mechanisms in the housing for retracting an actuator in the event of a failure. However, bailout mechanisms utilized in robotic surgical tools can present challenges, as they often require significant force to complete a bailout due to the coupling between the motors, drivers, and actuators. Various bailout mechanisms are therefore provided that allow direct engagement with one or more actuators to provide rapid and effective bailout (such as release, reversal, and/or retraction), while minimizing the amount of force and/or time to complete the bailout.

The systems, devices, and methods disclosed herein can be implemented using a robotic surgical system. As will be appreciated by a person skilled in the art, electronic communication between various components of a robotic surgical system can be wired or wireless. A person skilled in the art will also appreciate that all electronic communication in the system can be wired, all electronic communication in the system can be wireless, or some portions of the system can be in wired communication and other portions of the system can be in wireless communication.

FIG. 1 is a perspective view of one embodiment of a surgical robotic system 300 that includes a patient-side portion 310 that is positioned adjacent to a patient 312, and a user-side portion 311 that is located a distance from the patient, either in the same room and/or in a remote location. The patient-side portion 310 generally includes one or more robotic arms 320 and one or more tool assemblies 330 that are configured to releasably couple to a robotic arm 320. The user-side portion 311 generally includes a vision system 313 for viewing the patient 312 and/or surgical site, and a control system 315 for controlling the movement of the robotic arms 320 and each tool assembly 330 during a surgical procedure.

The control system 315 can have a variety of configurations and it can be located adjacent to the patient, e.g., in the operating room, remote from the patient, e.g., in a separate control room, or it can be distributed at two or more locations. For example, a dedicated system control console can be located in the operating room, and a separate console can be located in a remote location. The control system 315 can include components that enable a user to view a surgical site of a patient 312 being operated on by the patient-side portion 310 and/or to control one or more parts of the patient-side portion 310 (e.g., to perform a surgical procedure at the surgical site 312). In some embodiments, the control system 315 can also include one or more manually-operated input devices, such as a joystick, exoskeletal glove, a powered and gravity-compensated manipulator, or the like. These input devices can control teleoperated motors which, in turn, control the movement of the surgical system, including the robotic arms 320 and tool assemblies 330.

The patient-side portion can also have a variety of configurations. As depicted in FIG. 1, the patient-side portion 310 can couple to an operating table 314. However, in some embodiments, the patient-side portion 310 can be mounted to a wall, to the ceiling, to the floor, or to other operating room equipment. Further, while the patient-side portion 310 is shown as including two robotic arms 320, more or fewer robotic arms 320 may be included. Furthermore, the patient-side portion 310 can include separate robotic arms 320 mounted in various positions, such as relative to the surgical table 314 (as shown in FIG. 1). Alternatively, the patient-side portion 310 can include a single assembly that includes one or more robotic arms 320 extending therefrom.

Figure 2:
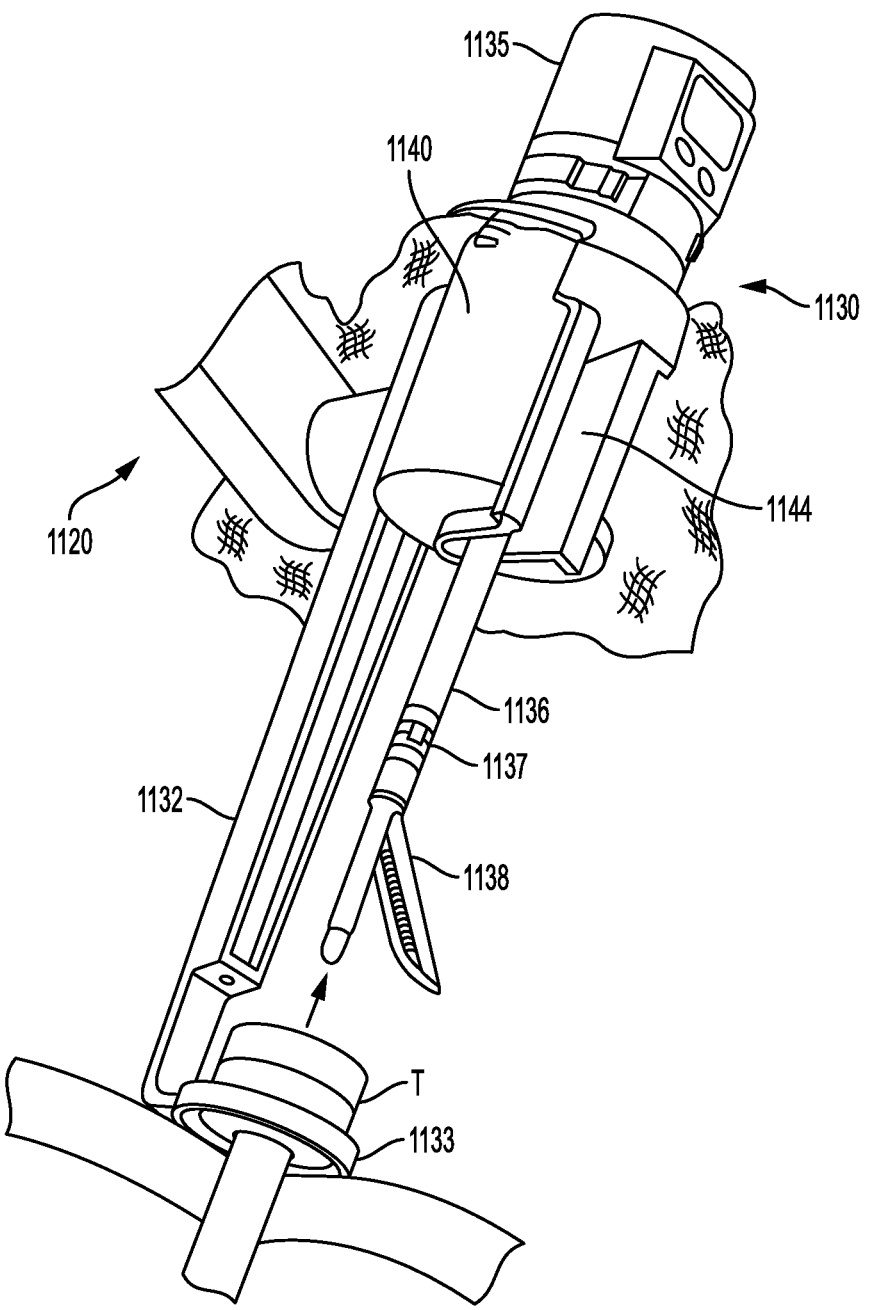
FIG. 2 is a perspective view of another embodiment of a surgical robotic system.

FIG. 2 illustrates another embodiment of a robotic arm 1120 and a tool assembly 1130 releasably coupled to the robotic arm 1120. The robotic arm 1120 can support and move the associated tool assembly 1130 along one or more mechanical degrees of freedom (e.g., all six Cartesian degrees of freedom, five or fewer Cartesian degrees of freedom, etc.).

The robotic arm 1120 includes a tool driver 1140 at a distal end of the robotic arm 1120, which can assist with controlling features associated with the tool assembly 1130. The robotic arm 1120 also include a tool guide 1132 that couples to a trocar T that is mated to a distal end feature 1133 (e.g., a ring) of the tool guide 1132. The tool guide 1130 holds the trocar to allow the shaft of the tool assembly 1130, which extends generally parallel to a threaded shaft of the tool guide 1132, to be advanced through and retracted from the trocar.

While the tool driver 1140 is not shown in detail, it generally includes one or more motors, e.g., seven motors, that control a variety of movements and actions associated with the tool assembly 1130. Each motor can be configured to couple to a drive assembly in the tool driver to thereby cause movement of a corresponding actuator, which in turn actuates the end effector. For example, actuation of one of the motors can rotate one or more gear assemblies, which in turn can cause linear and/or rotational movement of at least one actuator (e.g., gears, cables) extending through the tool shaft. Each actuator can cause actuation of the end effector, e.g., clamping, firing, rotating, articulation, etc.

As further shown in FIG. 2, the tool assembly 1130 can be loaded from a top side of the driver 1140 with the shaft of the tool assembly 1130 being positioned in a shaft-receiving channel 1144 formed along the side of the driver 1140. The shaft-receiving channel 1144 allows the shaft, which extends along a central axis of the tool assembly 1130, to extend along a central axis of the driver 1140 when the tool assembly 1130 is coupled to the driver 1140. In other embodiments, the shaft can extend through on opening in the tool driver 1140, or the two components can mate in various other configurations.

As shown in FIG. 2, the tool assembly 1130 includes a housing 1135 coupled to a proximal end of a shaft 1136 and an end effector 1138 coupled to a distal end of the shaft 1136. The housing 1135 can include coupling features that assist with releasably coupling the housing 1135 to the tool driver 1140 of the robotic arm 1120. The housing 1135 can include drivers (e.g., gears, shafts, cables etc.) that can be directly or indirectly actuated by the one or more motors in the tool driver. Each driving member in the housing 1135 can cause rotation or translation of an actuator (e.g., shaft, cable) extending through the elongate shaft and coupled to the end effector. Movement of the actuators can control the operation of various features associated with the end effector 1138 (e.g., clamping, firing, rotation, articulation, etc.), as well as control the movement of the shaft 1136 (e.g., rotation and/or articulation of the shaft).

The shaft 1136 can be releasably coupled to the housing 1135 such that the shaft 1136 can be interchangeable with other shafts. This can allow a single housing 1135 to be adaptable to various shafts 1136 having different end effectors 1138. The shaft 1136 can also include one or more joints or wrists 1137 that allow a part of the shaft 1136 or the end effector 1138 to rotate and/or articulate relative to the longitudinal axis of the shaft 1136. This can allow for fine movements and various angulation of the end effector 1138 relative to the longitudinal axis of the shaft 1136. The end effector 1138 can include any of a variety of surgical tools, such as a stapler, a clip applier, forceps, a needle driver, a cautery device, a cutting tool, a pair of jaws, an imaging device (e.g., an endoscope or ultrasound probe), or a combined device that includes a combination of two or more various tools.

Figure 3:
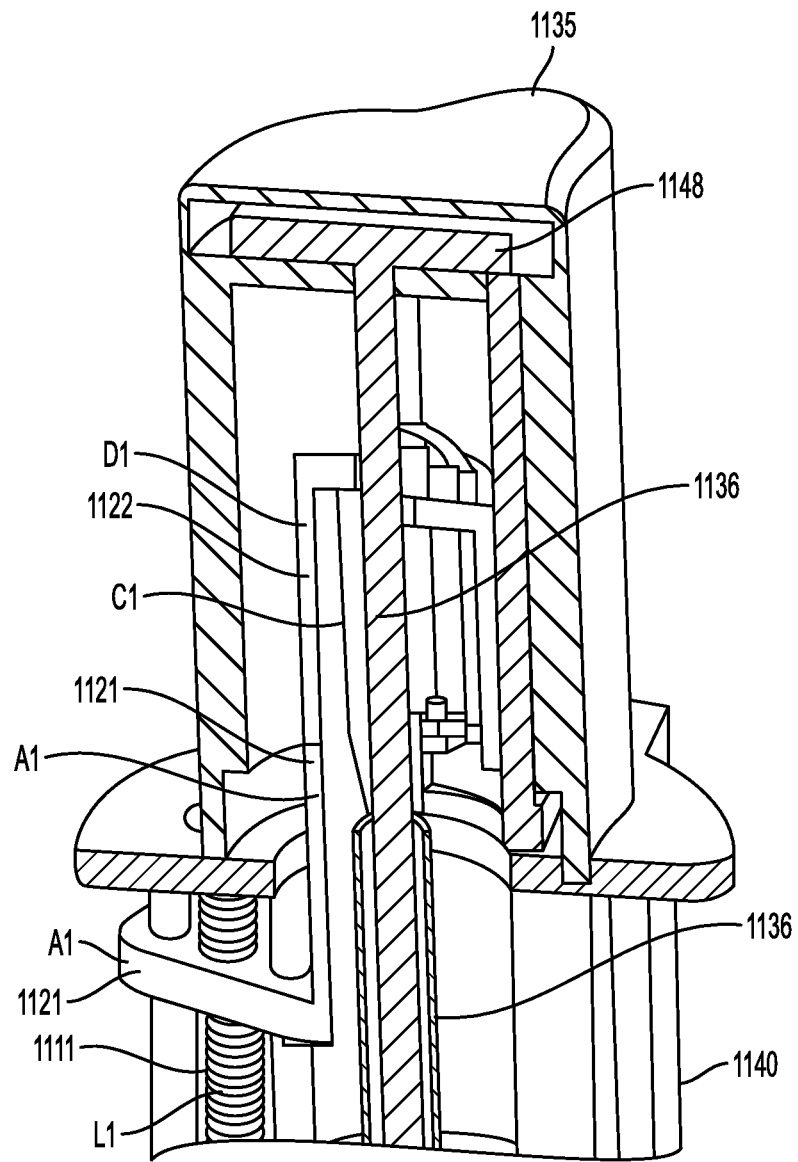
FIG. 3 is a perspective view of an interior of a tool housing and a tool driver of the surgical robotic system of FIG. 2.

FIG. 3 illustrates a portion of the housing 1135 coupled to a portion of the driver 1140 with the motors being configured to drive the drivers in the housing 1135. For example, the tool driver 1140 has a first motor (not shown) that drives rotation of a lead screw L1, which in turn causing an actuator A1, which is threadably coupled to lead screw L1, to linearly advance in the proximal direction (towards and into the housing 1135). Actuator A1 can include an extension threadably coupled to the lead screw L1. The extension can be coupled to or integrated with a partial cylindrical shaft that extends along the longitudinal axis of the tool housing 1135 and the tool driver 1140. The partial cylindrical shaft of the actuator A1 can engage with driving member D1 such that when the actuator A1 is linearly advanced, the driving member D1 is caused to linearly advance in the same direction. Driving member D1 can be coupled to an actuator extending through the tool shaft, such as cable C1, such that when driving member D1 is advanced in the proximal direction, cable C1 is pulled in the proximal direction. Cable C1 extends along the shaft of the tool assembly 1130 and is operatively coupled to a part of the end effector 1138 thereby controlling a function of the end effector 1138 (e.g., opening and closing of jaws, articulation, firing of one or more staples, etc.) when the cable is C1 translated in either the proximal or distal direction. Although the actuators in the tool driver and in the tool shaft are described as being linearly translated, the actuators can be linearly translated and/or rotationally moved as a result of actuation of a respective motor. Any number of motors can be included in the driver 1140 for actuating various aspects of the tool assembly 1130.

Figure 4:
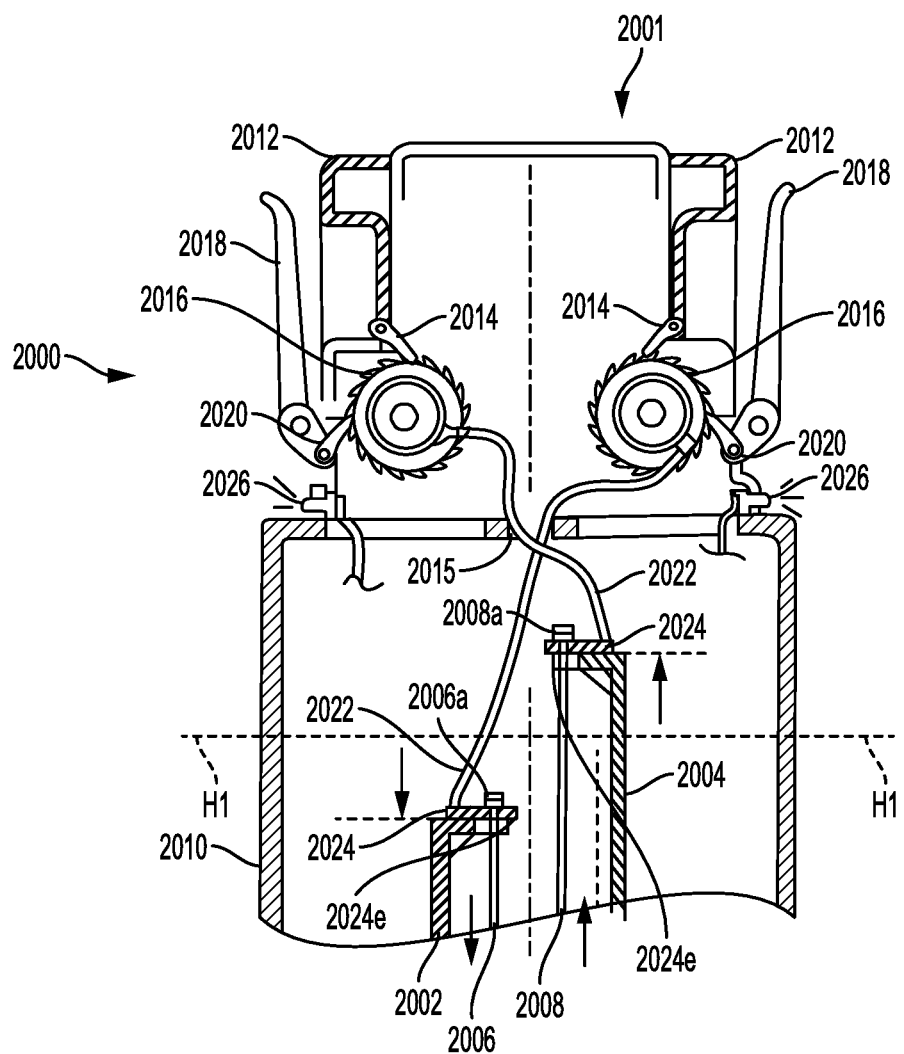
FIG. 4 is a cross-sectional side view of one embodiment of part of a surgical tool with an elongate shaft and a bailout mechanism.
Figure 5:
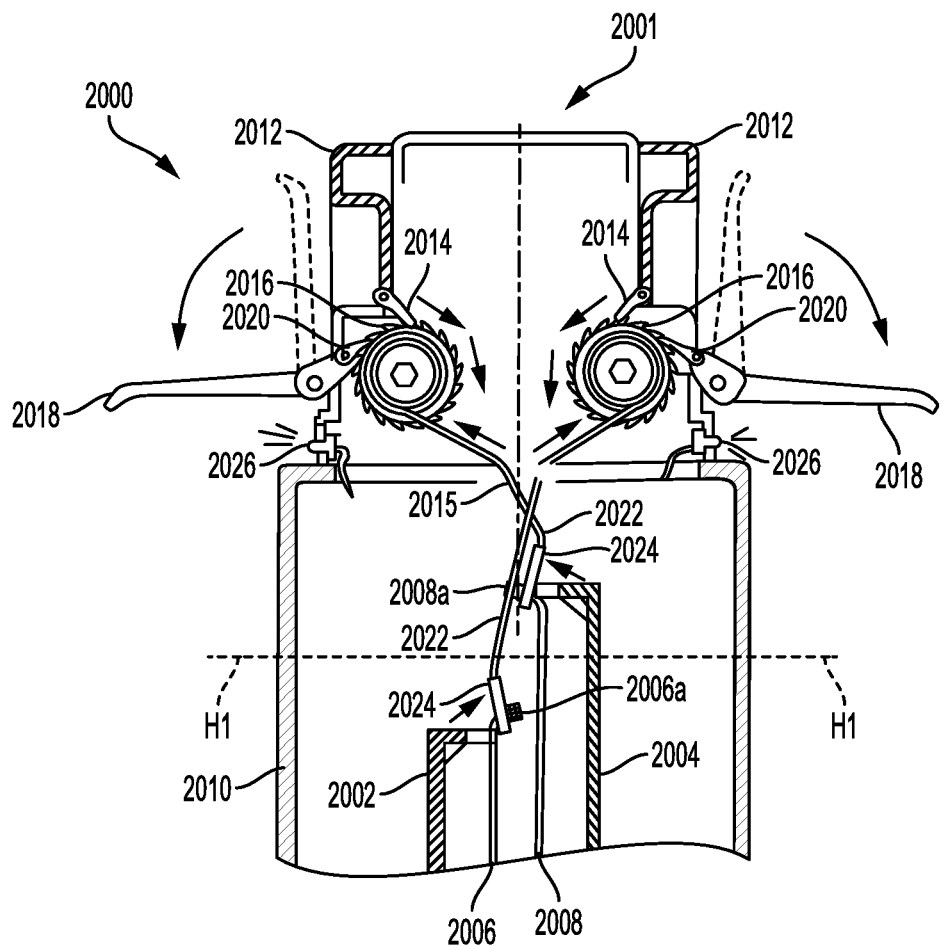
FIG. 5 is a cross-sectional side view of the surgical tool of FIG. 4.
Figure 6:
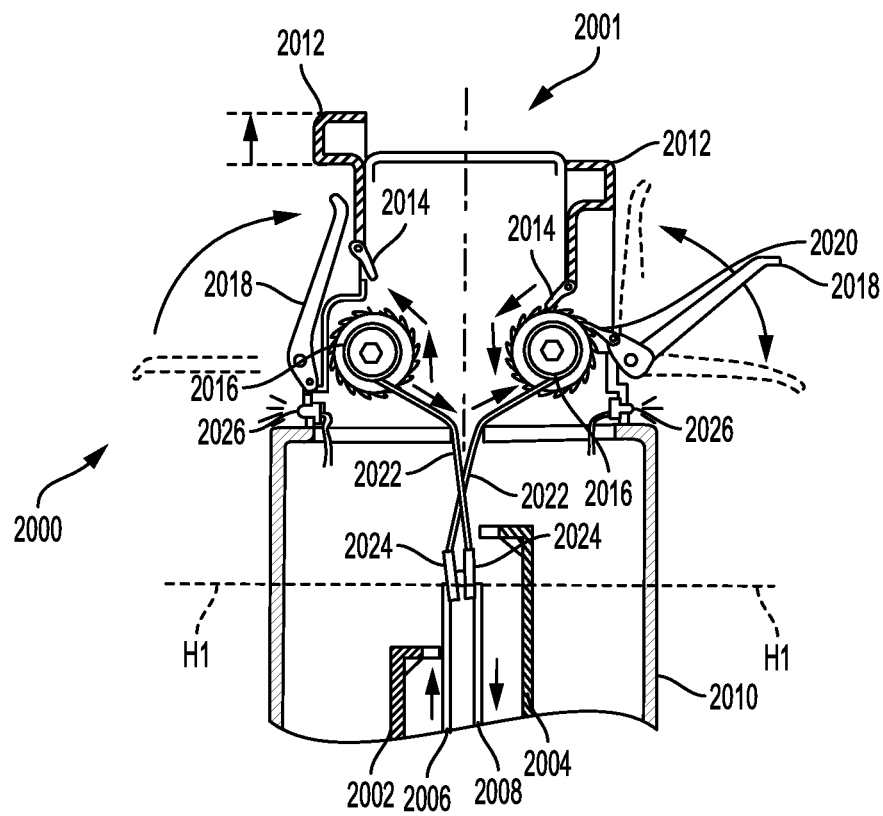
FIG. 6 is another cross-sectional side view of the surgical tool of FIG. 4.

FIGS. 4-6 illustrate a bailout assembly 2000 mounted to a proximal end of a tool housing, which can have the same configuration as tool housing 1135 of FIGS. 2-3. The tool housing includes actuation members or actuators, e.g., cables 2006, 2008 (similar to cable C1 of FIG. 3) that extend through the elongate shaft and couple to a feature associated with either the shaft 2010 or an end effector disposed on a distal end thereof, the cables 2006, 2008 to thereby control operation of various features associated with the shaft 2010 and/or an end effector. A proximal end of each cable 2006, 2008 is coupled to a driving member or driver 2002, 2004 (similar to the driver D1 of FIG. 3). The drivers 2002, 2004 can each be engaged with an actuator of the tool driver (such as actuator A1 of FIG. 3) such that actuation of a motor causes actuation of the drivers 2002, 2004. With the proximal end of each driving member 2002, 2004 being coupled to a proximal end of a cable 2006, 2008, proximal movement of the driving members 2002, 2004 pulls the cable 2006, 2008 coupled thereto proximally, to thereby actuate the end effector. For example, the cables 2006, 2008 can be articulation cables that are coupled to opposite sides of the end effector adjacent to a pivot joint or wrist. Proximal movement of one of the cables 2006 will cause the end effector to articulate in a first direction, and proximal movement of the other cable 2008 will cause the end effector to articulate in a second, opposite direction. In this case, the cables 2006, 2008 can control articulation in a single plane. However, a person skilled in the art will appreciate that the device can include any number of articulation cables for causing articulation in any number of directions. Moreover, the actuation members can have a variety of other configurations and can be used to affect any number of different motions of the end effector and/or shaft. For example, one of the actuation members can be coupled to a jaw of an end effector and proximal translation of the actuation member can be configured to pull the jaw from the open position to the closed position.

As indicated above, the bailout mechanism 2000 is mounted on the tool housing and includes a housing 2001 having one or more bailout levers in the form of crank arms 2018 coupled thereto. A person skilled in the art will appreciate that the device can include any number of bailout levers, and the number of levers will depend on the number of actuators in which mechanical bailout may be decided. Each bailout lever 2018 is configured to apply a direct force to an actuator extending through the tool shaft to thereby pull the actuator proximally, thus manually retracting the actuator and reversing a motion of the end effector. For example, where the actuator is an articulation cable, the bailout lever will be effective to retract the cable and return the end effector to a straight, non-articulated configuration. Where the actuator is a drive shaft that advances a sled through the end effector for firing staples from the end effector, the bailout lever will be effective to retractor the drive shaft and thereby pull the sled back to the initial position. Where the actuator is a closure tube that advances to close opposed jaws of an end effector, the bailout lever will be effective to retractor the closure tube thereby allowing the jaws to open. The bailout lever can be used for any number of actuation assemblies.

In the illustrated embodiment, the bailout assembly 2000 includes longitudinally slidable side walls 2012 disposed on opposite sides of the housing 2001. The side walls 2012 can be longitudinally slidably coupled to the housing 2001 by any number of mechanisms, such as grooves, channels, edging, tabs, etc. A first pawl 2014 is rotatably disposed on a proximal end of each of the slidable side walls 2012. Each of the first pawls 2014 engages a rotatable wheel or gear 2016 disposed within the housing 2001 adjacent to the proximal end of the tool housing 2010. The gears 2016 are each only rotatable in one direction, e.g. clockwise, when the first pawls 2014 are engaged with the gears, e.g., during normal operation of the device as discussed below. The gears 2016 also engage with second pawls 2020, each of which is coupled a crank arm 2018. The second pawls 2020 when engaged are configured to allow rotation of each of the gears 2016 only in the same direction as the first pawls 2014. The crank arms 2018 have a home position illustrated in FIG. 4 where each crank arm 2018 is approximately parallel to a longitudinal axis of the shaft 2010, an outward position illustrated in FIG. 5 where the crank arm 2018 is rotated to an approximately perpendicular position away from the shaft 2010, and an inward position illustrated in FIG. 6 where the crank arm 2018 is rotated toward the shaft 2010.

Bailout cables 2022 are coupled on a proximal end thereof to the gears 2018 and are each wound around the gears 2018. The bailout cables 2022 extend distally into the tool housing 2010 through an opening in a proximal end of the tool housing 2010 and are coupled on a distal end thereof to bailout plates 2024 that in turn couple to the proximal end of one of the cables 2006, 2008. The bailout cables 2022 cross each other such that they extend from the gears 2018 to an opposite side of the longitudinal axis of the shaft 2010 to mate to the bailout plates 2024. The bailout plates 2024 extend along a proximal surface of each of the driving members 2002, 2004 prior to activation of the bailing assembly. The bailout cables 2022 are configured to translate linearly along the longitudinal axis of the shaft 2010. The bailout plates 2024 of the bailout cables 2022 are non-removably coupled to each of the cables 2006, 2008. For example, the cables 2006, 2008 can pass through a hole in the plates 2024 and can include a bulge 2006a, 2008a on a proximal end thereof that is too large to pass through the hole. However, a variety of coupling means are possible, such as crimping, tying, pressing, welding, etc.

Figure 7A:
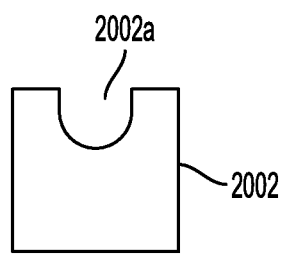
FIG. 7a is a top down view of a driving member of the surgical tool of FIG. 6.
Figure 7B:
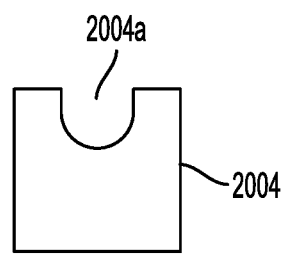
FIG. 7b is a top down view of another driving member of the surgical tool of FIG. 6.

The proximal end of each driving member 2002, 2004 is removably coupled to the proximal end of each cable 2006, 2008. For example, the proximal end of each driving member 2002, 2004 can include a u-shaped notch 2002a, 2004a, as illustrated in FIGS. 7a and 7b. Each cable 2006, 2008 can be positioned within the u-shaped notch 2002a, 2004a with each corresponding bailout plate 2024 resting on top of the proximal ends of each driving member 2002, 2004 during normal operation of the device.

LED lights 2026 can be disposed at a distal end of the bailout mechanism 2000, and each LED light 2026 can be electronically coupled to the device. The LED lights 2026 can be coupled to a control system, such as the control system 315 discussed herein. During operation of the device, the LED lights can be configured to indicate a status of the driving members 2002, 2004. For example, if there is a mechanical failure such as with one of the driving members 2002, 2004 and/or there is some other error requiring bailout, the LED lights 2026 can be configured to blink or otherwise indicate a location of the failure and/or error. Error locations can be identified in a variety of ways, as further explained in U.S. patent application Ser. No. 15/131,963, filed on Apr. 18, 2016 and entitled "Method for Operating a Surgical Instrument," which is hereby incorporated herein by reference in its entirety.

During normal operation of the device, the driving members 2002, 2004 can translate linearly to manipulate the cables 2002, 2004, thereby actuating the end effector. The bailout cables 2022 have enough slack to translate with the driving members 2002, 2004 and the cables 2002, 2004. For example, as illustrated in FIG. 3, driving member 2002 and actuation cable 2006 are advanced distally from a home position H1 while driving member 2004 and actuation cable 2008 are retracted proximally from the home position F11, for example while performing articulation of the shaft 2010. The bailout cables 2022 move distally and proximally with the corresponding driving members 2002, 2004 and cables 2006, 2008.

If a failure occurs, for example if one or both of the driving members 2002, 2004 experience a mechanical failure, the bailout mechanism 2000 can be used to bailout the device. As illustrated in FIG. 5, the crank arm 2018 can be repeatedly rotated to the outward position to cause the second pawl 2020 coupled thereto to rotate the gear 2016, e.g., in the clockwise direction. Turning the gear 2016 causes the bailout cable 2022 to wind around the gear and thereby retract proximally. This will in turn apply a proximal force to the bailout plate 2024, causing an end of the plate 2024 (opposite to the end having the bailout cable 2022 attached thereto) to be pulled upward such that the plate 2024 pivots, as shown in FIG. 5. Continued proximal movement of the plate 2024 will pull the actuation cable 2006 or 2008 out of the u-shaped notches on the driving member 2002, 2004, as illustrated in FIG. 6. The cable 2006 or 2008 is thus pulled free from the opening in the u-shaped notch 2002a or 2004a on the driving member 2002 or 2004.

When the cable 2006 or 2008 is disengaged from the driving member 2002 or 2004, as illustrated in FIG. 6, the gear 2016 can either be released to free a retracted cable, or rotated to retract an advanced cable. For example, to return actuation cable 2008 to the home position, the crank arm 2018 coupled thereto can be rotated toward the shaft 2010 into the inward position, as shown in FIG. 6, to cause the second pawl 2020 to disengage from the gear 2016. The side wall 2012 can be manually moved proximally, disengaging the first pawl 2014 from the gear 2016. When the gear 2016 is disengaged from the pawls 2014, 2020, the gear 2016 is freely rotatable. This will allow the retracted actuation cable 2008 to freely move linearly in a distal direction and thereby return to the home position. In order to return actuation cable 2006 to the home position, the crank arm 2018 coupled thereto can then be repeatedly rotated toward the shaft 2010 to rotate the gear 2016 and wind up the bailout cable 202, thereby pulling the advanced actuation cable 2006 coupled thereto back to the home position. The pawls 2014, 2020 will work in unison to prevent the gear 2016 from rotating in an opposite direction. The corresponding LED light 2026 can indicate when each cable 2006, 2008 is in the home position. Accordingly, the bailout assembly allows an actuator to be disengaged from the drive assembly and to be directly manually retracted.

Figure 8:
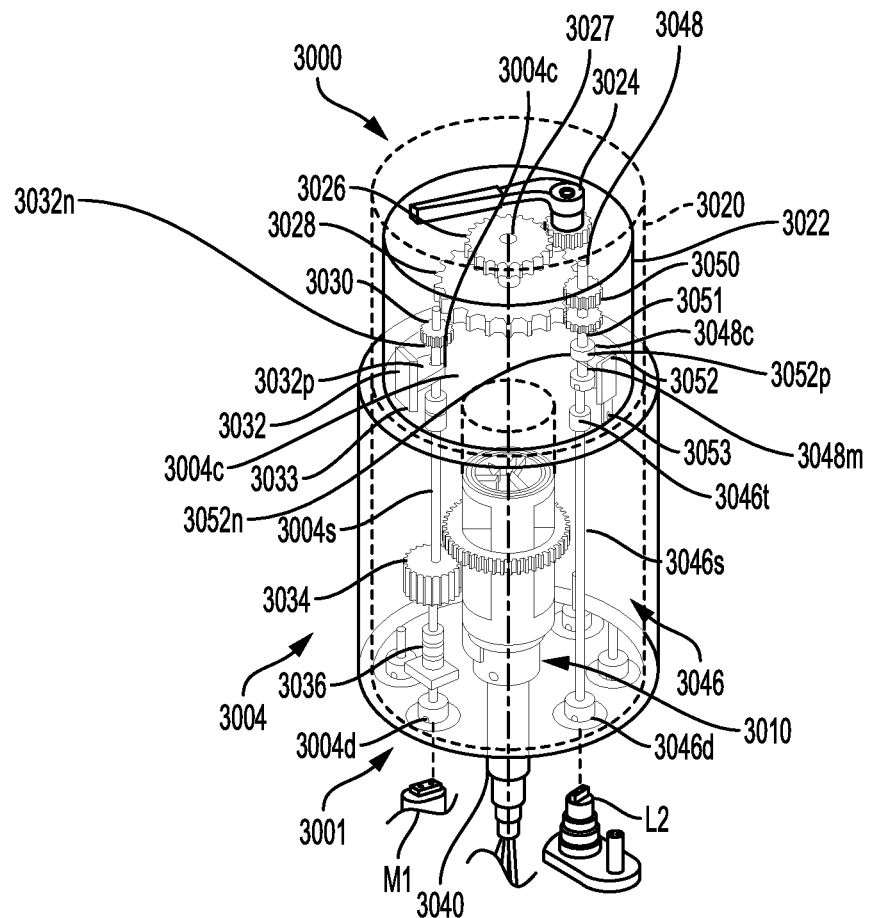
FIG. 8 is a partially transparent perspective view of another embodiment of a bailout mechanism on a surgical tool.
Figure 9:
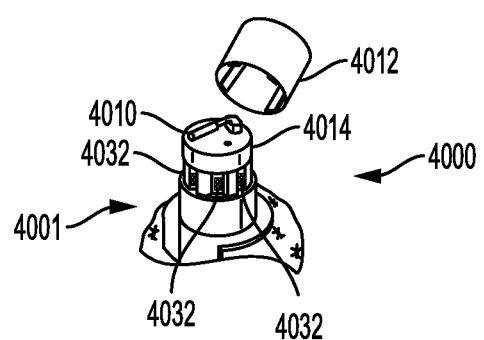
FIG. 9 is a perspective view of another embodiment of a bailout mechanism on a surgical tool.

FIG. 8 illustrates another embodiment of a bailout mechanism 3000 coupled to a tool housing 3001, and FIG. 9 illustrates a similar bailout mechanism 4000 coupled to a tool housing 4001. The tool housings 3001, 4001 can be similar to the tool housing 1135 of FIGS. 2-3. As shown, the tool housing 3001 includes drive assemblies disposed therein and configured to couple to one or more motors in the tool driver (e.g., tool driver 1140 of FIG. 2). In the illustrated embodiment, there are seven drive assemblies (only two are shown) that couple to several motors in the tool driver. Each drive assembly is configured to control an actuation member extending through the elongate shaft for actuating the end effector and/or the shaft, e.g., for causing rotation, articulation, clamping, firing, etc. A person skilled in the art will appreciate that the tool housing can include any number of drive assemblies, and the number may vary depending on the particular tool and the actuation members needed to operate the end effector.

In the illustrated embodiment, a first drive assembly 3004 includes a coupling 3004d for connecting to a motor M1. A second drive assembly 3046 includes a coupling 3046d for connecting to a lead screw L2. In the bailout mechanism 3000, there are two bailouts illustrated, one for the first drive assembly 3004 with a drive shaft 3004s and the other for the second drive assembly 3046 with a drive shaft 3046s. Separate bailouts can be provided for each function (e.g. clamping, firing, rotation, actuation, etc.), and the two illustrated bailouts are exemplary bailouts that can be applied to any or all drive assemblies. The bailout mechanism 3000 has a removable cover 3020 and an inner cover 3022. Extending through a proximal surface of the inner cover 3022 is a hand crank 3024. The hand crank 3024 engages a gear which engages a first primary bailout drive gear 3026, which in turn is non-removably coupled to a second primary bailout drive gear 3028 by a drive shaft 3027. Thus rotation of the hand crank 3024 ultimately causes rotation of the second primary bailout drive gear 3028.

Regarding the bailout for the first drive assembly 3004, a spur gear 3030 is located on a proximal end of the drive shaft 3004s. A bailout switch 3032 extends through the inner cover 3022 and is coupled to the drive shaft 3004s. The bailout switch 3032 is longitudinally slidably disposed within grooves formed in the cover 3022. The switch 3032 couples to the drive shaft 3004s by a perpendicular extension 3032p that extends between the cover 3022 and the drive shaft 3004s. The perpendicular extension 3032p of the switch 3032 has a notch 3032n on an end thereof through which the drive shaft 3004s passes. The drive shaft 3004s has a circular portion 3004c with a diameter greater than the rest of the drive shaft 3004s and greater than a diameter of the notch 3032n of the switch 3032 such that the circular portion 3004c engages and rests distally to the perpendicular extension 3032p of the switch 3032. An LED light 3033 can be disposed on the inner cover 3022 adjacent to the bailout switch 3032 through a variety of means, such as gluing, screwing, or embedding by compression fit the LED light 3033 through a hole in the cover 3022. The LED light 3033 can be coupled to a control system, such as the control system 315 discussed herein. A gear 3034 is fixed on the drive shaft 3004s and has teeth thereon that engage an actuator 3010 that extends through a shaft 3040 and that can actuate various features associated with the shaft 3040 and/or an end effector that can be disposed on a distal end of the shaft 3040, similar to a functionality of the cable C1 of FIG. 3. A spring 3036 is disposed on a distal end of the drive shaft 3004s, and the drive shaft 3004s couples to the motor M1 at a distalmost end thereof through the coupling 3004d. A tooth on the motor M1 engages a groove on the coupling 3004d. The spring 3036 biases the drive shaft 3004s proximally.

During normal operation, the spring 3036 is kept in a compressed state, and the bailout switch 3032 is configured to apply distal pressure to the drive shaft 3004s to keep the drive shaft 3004s engaged with the motor M1. The drive shaft 3004s will rotate with rotation of the motor M1, which will cause rotation of the gear 3034 and subsequently cause driving of the actuator 3010 through one or more additional gears. The switch 3032 applies distal pressure by the perpendicular extension 3032p and the notch 3032n of the switch 3032 applying distal force to the circular portion 3004c on the drive shaft 3004s. The LED light 3033 can indicate a normal status of the bailout switch 3032 (i.e. when bailout has not been actuated) and/or one or more actuators of the surgical tool by blinking, remaining on, remaining off, displaying a particular color such as green, etc., as discussed in U.S. patent application Ser. No. 15/131,963, filed on Apr. 18, 2016 and entitled "Method for Operating a Surgical Instrument," incorporated herein by reference.

When bailout is desired, the switch 3032 is actuated by manually sliding the switch 3032 proximally. The perpendicular extension 3032p and the notch 3032n of the switch 3032 will slide proximally, which will allow the circular portion 3004c on the drive shaft 3004s to move proximally because the spring 3036 will force the drive shaft 3004s proximally as the spring 3036 decompresses and biases the drive shaft 3004s proximally. Proximal movement of the drive shaft 3004s moves the coupling 3004d out of engagement with the motor M1. So any further rotation of the motor M1 will no longer rotate the drive shaft 3004s. The gear 3034 on the drive shaft 3004s will remain engaged with the actuator 3010 even with proximal movement because the gear 3034 is generally elongate in length such that the teeth of the gear 3034 will move proximally along the actuator 3010 while remaining engaged therewith. The spur gear 3030 will move proximally with the drive shaft 3004s, bringing the spur gear 3030 into engagement with the second primary bailout drive gear 3028. The bailout hand crank 3024 can then be manually rotated to apply rotational movement to the first primary bailout drive gear 3026, which will rotate the drive shaft 3027 and the second primary bailout drive gear 3028. The second primary bailout drive gear 3028 will in turn rotate the spur gear 3030. Rotation of the spur gear 3030 will rotate the drive shaft 3004s, which will rotate the gear 3034. The gear 3034 will rotate the actuator 3010 and subsequently cause retraction and/or reversal of various features associated with the shaft 3040 and/or the end effector that can be disposed on the distal end of the shaft 3040, similar to the functionality of the cable C1 of FIG. 3. Thus rotation of the drive shaft 3004s can cause reversal through bailout of actuators driven by a motor and responsible for a variety of functions, such as cutting and/or grasping tissue. The LED light 3033 can optionally be used to indicate an error status of the bailout switch 3032 (i.e. when bailout has been actuated) and/or one or more of the actuators in the surgical tool by blinking, flashing, remaining on, displaying a particular color such as red, etc., as discussed in U.S. patent application Ser. No. 15/131,963, filed on Apr. 18, 2016 and entitled "Method for Operating a Surgical Instrument," incorporated herein by reference.

Regarding the bailout for the second drive assembly 3046, a top bailout rod 3048 is disposed in the inner cover 3022 directly proximal to a bottom bailout rod 3046s. On a proximal end of the top bailout rod 3048 is a spur gear 3050. A spring 3051 is disposed on the bailout rod 3048. A bailout switch 3052 is coupled to the top bailout rod 3048 and is configured to apply a proximal force on the top bailout rod 3048. The bailout switch 3052 extends through the inner cover 3022. The bailout switch 3052 is longitudinally slidably disposed within a groove formed in the cover 3022. The switch 3052 couples to the top bailout rod 3048 by a perpendicular extension 3052p that extends between the cover 3022 and the top bailout rod 3048. The perpendicular extension 3052p of the switch 3052 has a notch 3052n on an end thereof through which the top bailout rod 3048 passes. The top bailout rod 3048 has a circular portion 3048c with a diameter greater than the rest of the top bailout rod 3048 and greater than a diameter of the notch 3052n of the switch 3052 such that the circular portion 3048c engages and rests proximally to the perpendicular extension 3052p of the switch 3052. An LED light 3053 can be disposed on the inner cover 3022 adjacent to the bailout switch 3052 through a variety of means, such as gluing, screwing, or embedding by compression fit the LED light 3053 through a hole in the cover 3022. The LED light 3053 can be coupled to a control system, such as the control system 315 discussed herein. The top bailout rod 3048 has a coupling mechanism 3048m in the form of a groove on a distal end thereof that is configured to engage a coupling mechanism 3046t in the form of a tooth on a proximal end of the bottom bailout rod 3046s. The coupling 3046d in the form of a groove on a distalmost end of the bottom bailout rod 3046s is configured to engage a tooth of the lead screw L2.

During normal operation, the spring 3051 is kept in a compressed state, and the bailout switch 3052 is configured to apply proximal pressure to the circular portion 3048c of the top bailout rod 3048 to keep the spur gear 3050 held proximally and thus disengaged from the second primary bailout drive gear 3028. With the top bailout rod 3048 held proximally by the bailout switch 3052, the top bailout rod 3048 is disengaged with the bottom bailout rod 3046s, and the bottom bailout rod 3046s is disengaged from the lead screw L2.

When bailout is desired, the switch 3052 is actuated by manually sliding the switch 3052 distally. The perpendicular extension 3052p and the notch 3052n of the switch 3052 will move distally, which will allow the circular portion 3048c of the top bailout rod 3048 to move distally because the spring 3056 will force the top bailout rod 3048 distally as the spring 3056 decompresses and biases the top bailout rod 3048 distally. Distal movement of the top bailout rod 3048 moves the coupling mechanism 3048m distally into engagement with the coupling mechanism 3046t of the bottom bailout rod 3046s while forcing the bottom bailout rod 3046s distally itself. The coupling 3046d on the distalmost end of the bottom bailout rod 3046s is then brought into engagement with the lead screw L2 as the bottom bailout rod 3046s moves distally. The spur gear 3050 will thus move distally with the top bailout rod 3048, bringing the spur gear 3050 into engagement with the second primary bailout drive gear 3028. The bailout hand crank 3024 can then be manually rotated to apply rotational movement to the first primary bailout drive gear 3026, which will rotate the drive shaft 3027 and the second primary bailout drive gear 3028. The second primary bailout drive gear 3028 will in turn rotate the spur gear 3050. Rotation of the spur gear 3050 will rotate the top bailout rod 3048, which will rotate the bottom bailout rod 3046s and that will in turn rotate the lead screw L2. Rotation of the lead screw L2 will subsequently cause retraction and/or reversal of various features associated with the shaft 3040 and/or the end effector disposed on the distal end of the shaft 3040, similar to a functionality of cable C1 of FIG. 3. For example, a lead screw can cause linear and/or rotational movement of at least one actuator responsible for controlling one or more actions and movements, such as articulation, which can be reversed through bailout. The LED light 3053 can optionally be used to indicate an error status of the bailout switch 3052 (i.e. when bailout has been actuated) and/or one or more of the actuators in the surgical tool by blinking, flashing, remaining on, displaying a particular color such as red, etc., as discussed in U.S. patent application Ser. No. 15/131,963, filed on Apr. 18, 2016 and entitled "Method for Operating a Surgical Instrument," incorporated herein by reference.

While the bailout switches are represented as tabs, the switches can take a variety of forms, such as switches, plugs, closures, pressure points, etc. For example, as seen in FIG. 9, a plurality of bailout switches 4032 can be provided in the form of pull tabs. FIG. 9 further illustrates a hand crank 4010, a removable outer cover 4012, an inner cover 4014, and LED lights 4016 similar to the bailout mechanism 3000 of FIG. 8, and the bailout mechanism 4000 can operate similar to the bailout mechanism 3000 of FIG. 8. The bailout mechanisms 3000, 4000 are selective bailout mechanisms, allowing individual actuators to be bailed out. Thus select features and functions of any shaft and/or any end effector disposed on a distal end of the shaft can be reversed, retracted, and/or bailed out.

Figure 10:
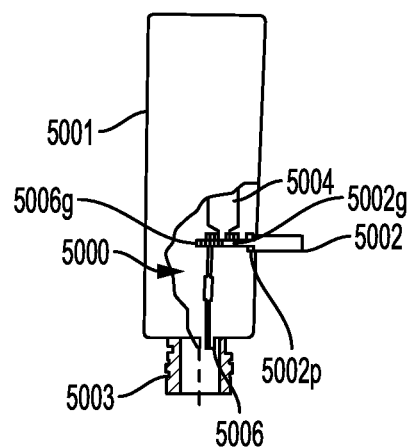
FIG. 10 is a side view that has been partially cut away of another embodiment of a bailout mechanism on a surgical tool.

FIGS. 10-13 illustrate additional embodiments of bailout mechanism 5000, 6000, and 7000. The bailout mechanisms 5000, 6000, and 7000 can be coupled to a tool housing actuation assembly, such as the tool housing actuation assembly contained within the housing 1135 of FIGS. 2-3. The bailout mechanisms 5000, 6000, and 7000 are similar to the bailout mechanisms 3000, 4000 of FIGS. 8-9 but provide single-actuator (and often single-function) bailout mechanisms rather than allowing selection of actuator(s) as in the bailout mechanisms 3000, 4000. FIG. 10 illustrates a bailout mechanism 5000 on a tool housing 5001 with an elongate shaft 5003 and a bailout lever 5002 coupled to a large motor 5004 and an actuator 5006. The motor 5004 has gear teeth that engage with a gear 5006g attached to a proximal end of the actuator 5006. The bailout lever 5002 has two positions, a first position in which the lever 5002 is held in a recessed part of a housing 5001c of the tool housing 5001 and a second position in which the lever 5002 is pivoted away from the housing 5001c about a pivot 5002p. The lever 5002 passes through the housing 5001c of the tool housing 5001 and has a ratchet and gear mechanism 5002g with teeth that engage the gear 5006g upon pivoting the lever 5002 into the second position. When the lever 5002 is in the second position and the ratchet and gear mechanism 5002g has engaged the gear 5006g, the lever 5002 is configured to be pivoted back and forth about the pivot 5002p to provide rotation to the gear 5006g. Under normal operation, the lever 5002 is in the first position recessed in the housing 5001c. The motor 5004 can be driven, which will thus rotate the gear 5006g and the actuator 5006 and cause actuation of a function on a distal end of the elongate shaft 5003 and/or an end effector (not shown) on a distal end of the elongate shaft 5003. When bailout is desired (such as after a malfunction in the elongate shaft and/or the end effector), the bailout lever 5002 can be pivoted into the second position. Manually pivoting the bailout lever 5002 will cause the ratchet and gear mechanism 5002g to rotate the gear 5006g, thus rotating and reversing the actuator 5006. The functionality actuated by the actuator 5006 is thus reversed as long as a user continues to pivot the bailout lever 5002.

Figure 11:
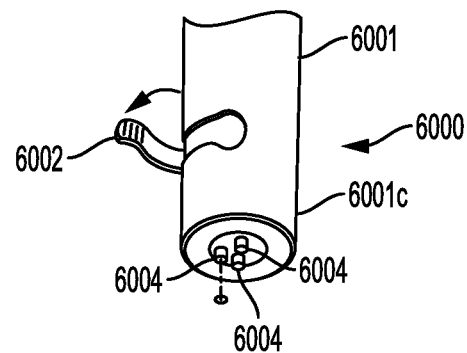
FIG. 11 is a perspective view of an embodiment of a bailout mechanism on a surgical tool.

The bailout mechanism 6000 of FIG. 11 is on a tool housing 6001 and is similar to the bailout mechanism 5000 of FIG. 10, containing a bailout lever 6002 and a plurality of actuators 6004. As with the bailout mechanism 5000, under normal operation the bailout lever 6002 is recessed in a housing 6001c of the tool housing 6001 and a motor and gear combination (not shown but similar to that of FIG. 10) rotate the actuators 6004 to perform various functions on an elongate shaft (not shown) and/or an end effector (not shown). When bailout is desired, the bailout lever 6002 is manually pivoted away from the housing 6001c. Upon continued pivoting of the lever 6002, a ratchet and gear mechanism (not shown but similar to that of FIG. 10) rotates one of the actuators 6004, causing the one or more functions of the actuator 6004 to be reversed.

Figure 12:
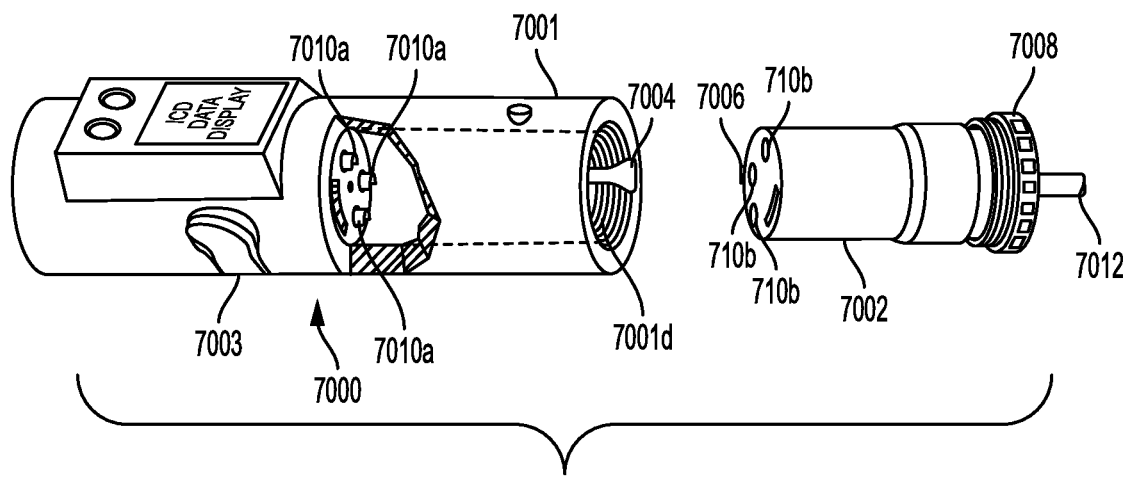
FIG. 12 is a perspective view that has been partially cut away of an embodiment of a bailout mechanism on a surgical tool.

The bailout mechanism 7000 of FIG. 12 is on a tool housing 7001 and is similar to the bailout mechanisms 5000, 6000, containing a bailout lever 7003 and a plurality of drivers 7010a. A tool 7002 is configured to be received in a channel 7001d of the tool housing 7001. The tool 7002 has actuators 7010b configured to engage the drivers 7010a through a groove and tooth engagement and configured to perform various functions on an elongate shaft 7012 and/or an end effector (not shown) on a distal end of the elongate shaft 7012. An alignment feature 7004 can be formed in the tool housing 7001 and configured to mate with a corresponding alignment feature 7006 on the tool 7002 that is configured to be mated with the tool housing 7001 and has a coupling ring 7008 and a shaft 7012 on a distal end thereof.

As with the bailout mechanisms 5000, 6000, under normal operation the bailout lever 7002 is recessed in a housing 7001 c of the tool housing 7001 and a motor and gear combination (not shown but similar to that of FIG. 10) rotate the drivers 7010a, which rotate the actuators 7010b to perform various functions on the elongate shaft 7012 and/or the end effector. When bailout is desired, the bailout lever 7002 is manually pivoted away from the housing 7001c. Upon continued pivoting of the lever 7002, a ratchet and gear mechanism (not shown but similar to that of FIG. 10) rotates one of the drivers 7010a, which rotates one of the actuators 7010b and causes the one or more functions of the one actuator 7010b to be reversed.

Figure 13:
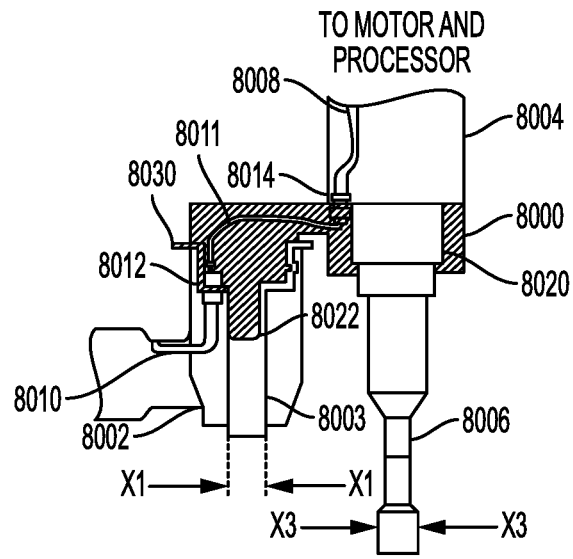
FIG. 13 is a partially cross-sectional side view of an embodiment of an adapter with a robotic arm and a surgical tool.

While bailouts operate on various tool assemblies, in some embodiments it can be difficult or impossible to couple various tool assemblies to select robotic arms given sizes and dimensions of the various tool assemblies compared to the select robotic arms. Adapters can thus be provided when tool assemblies and robotic arms could not otherwise be coupled together. FIG. 13 illustrates a lateral adapter 8000. A robotic arm 8002 (similar to the robotic arm 1120) and a tool assembly 8004 (similar to the tool assembly 1130) are provided, but the robotic arm 8002 and the tool assembly 8004 cannot be releasably coupled together under normal circumstances.

The tool assembly 8004 has an elongate shaft 8006 with a head having a distal diameter X3. The robotic arm 8002 has an opening 8003 configured to receive a shaft of a tool assembly with a maximum diameter X1, which is less than X3. The lateral adapter 8000 is thus provided having a receiving portion 8020 configured to receive the tool assembly 8004 at a location displaced laterally from an extension portion 8022 of the adapter 8000 that is configured to couple to and extend at least partially through the opening 8003 of the robotic arm 8002. The robotic arm has cables 8010 that couple at a contact point 8012 to cables 8011 in the adapter 8000, which in turn couple at a contact point 8014 to cables 8008 within the tool assembly 8004. Any control signals and/or power can travel between the robotic arm 8002 and the tool assembly 8004 along the cables 8008, 8010, 8011. A sterile barrier 8030 can be provided between the robotic arm 8002 on one side and the adapter 8000 and the tool assembly 8004 on another side in order to provide a sterile operation area while using the surgical system.

When the diameter X3 is greater than the diameter X1, the lateral adapter 8000 may allow the tool assembly 8004 and the robotic arm 8002 to couple together even though, as discussed, the robotic arm 8002 and the tool assembly 8004 cannot be releasably coupled together by passing the tool assembly 8004 through the robotic arm 8002.

Figure 14:
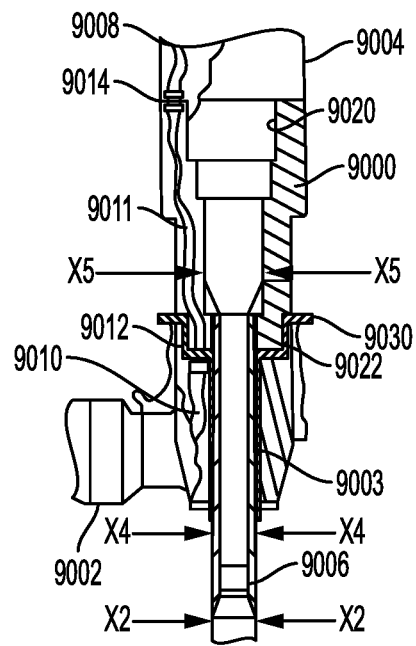
FIG. 14 is a partially cross-sectional side view of an embodiment of an adapter with a robotic arm and a surgical tool.

FIG. 14 illustrates another embodiment of an adaptor. In this embodiment, the adaptor is a vertical adapter 9000, rather than a lateral adapter. A tool assembly 9004 has an elongate shaft 9006 with a head having a distal diameter X2 and a body having a diameter X5. A robotic arm 9002 (similar to the robotic arm 8002) has an opening 9003 configured to receive a shaft of a tool assembly with a maximum diameter X4. The adapter 9000 has a receiving portion 9020 configured to receive the tool assembly 9004. The receiving portion 9020 is displaced vertically from an extension portion 9022 of the adapter 9000 that is configured to couple to and extend at least partially through the opening 9003 of the robotic arm 9002. The robotic arm has cables 9010 that couple at a contact point 9012 to cables 9011 in the adapter 9000 that in turn couple at a contact point 9014 to cables 9008 within the tool assembly 9004. Any control signals and/or power can travel between the robotic arm 9002 and the tool assembly 9004 along the cables 9008, 9010, 9011. A sterile barrier 9030 can be provided between the robotic arm 9002 on one side and the adapter 9000 and the tool assembly 9004 on another side in order to provide a sterile operation area while using the surgical system.

In this embodiment, the diameter X2 of the head of the tool assembly 9004 can be less than the diameter X4 of the opening 9003 of the robotic arm 9002, thus allowing the head of the tool assembly 9004 to pass through the opening 9003 of the robotic arm 9002. The diameter X5 of the body of the tool assembly 9004 is greater than the diameter X4, however, thus preventing the tool assembly 9004 from fully engaging with the robotic arm 9002. The vertical adapter 9000 may consequently allow the tool assembly 9004 and the robotic arm 9002 to couple together even though, as provided, the robotic arm 9002 and the tool assembly 9004 cannot be releasbly coupled together by sitting the tool assembly 8004 fully into the opening 9003 of the robotic arm 9002.

There are several general aspects that apply to the various descriptions herein. For example, at least one surgical end effector is shown and described in various figures. An end effector is the part of a surgical instrument or assembly that performs a specific surgical function, e.g., forceps/graspers, needle drivers, scissors, electrocautery hooks, staplers, clip appliers/removers, suction tools, irrigation tools, etc. Any end effector can be utilized with the surgical systems described herein. Further, in exemplary embodiments, an end effector can be configured to be manipulated by a user input tool. The input tool can be any tool that allows successful manipulation of the end effector, whether it be a tool similar in shape and style to the end effector, such as an input tool of scissors similar to end effector scissors, or a tool that is different in shape and style to the end effector, such as an input tool of a glove dissimilar to end effector graspers, and such as an input tool of a joystick dissimilar to end effector graspers. In some embodiments, the input tool can be a larger scaled version of the end effector to facilitate ease of use. Such a larger scale input tool can have finger loops or grips of a size suitable for a user to hold. However, the end effector and the input tool can have any relative size.

A slave tool, e.g., a surgical instrument, of the surgical system can be positioned inside a patient's body cavity through an access point in a tissue surface for minimally invasive surgical procedures. Typically, cannulas such as trocars are used to provide a pathway through a tissue surface and/or to prevent a surgical instrument or guide tube from rubbing on patient tissue. Cannulas can be used for both incisions and natural orifices. Some surgical procedures require insufflation, and the cannula can include one or more seals to prevent excess insufflation gas leakage past the instrument or guide tube. In some embodiments, the cannula can have a housing coupled thereto with two or more sealed ports for receiving various types of instruments besides the slave assembly. As will be appreciated by a person skilled in the art, any of the surgical system components disclosed herein can have a functional seal disposed thereon, therein, and/or therearound to prevent and/or reduce insufflation leakage while any portion of the surgical system is disposed through a surgical access port, such as a cannula. The surgical systems can also be used in open surgical procedures. As used herein, a surgical access point is a point at which the slave tool enters a body cavity through a tissue surface, whether through a cannula in a minimally invasive procedure or through an incision in an open procedure.

The systems, devices, and methods disclosed herein can be implemented using one or more computer systems, which may also be referred to herein as digital data processing systems and programmable systems.

One or more aspects or features of the subject matter described herein can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computer system may include clients and servers. A client and server are generally remote from each other and typically interact through a communication network. The relationship of client and server arises by virtue of computer programs running on the respective computers and having a client-server relationship to each other.

The computer programs, which can also be referred to as programs, software, software applications, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example as would a processor cache or other random access memory associated with one or more physical processor cores.

To provide for interaction with a user, one or more aspects or features of the subject matter described herein can be implemented on a computer having a display device, such as for example a cathode ray tube (CRT) or a liquid crystal display (LCD) or a light emitting diode (LED) monitor for displaying information to the user and a keyboard and a pointing device, e.g., a mouse, a trackball, etc., by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including, but not limited to, acoustic, speech, or tactile input. Other possible input devices include, but are not limited to, touch screens or other touch-sensitive devices such as single or multi-point resistive or capacitive trackpads, voice recognition hardware and software, optical scanners, optical pointers, digital image capture devices and associated interpretation software, and the like.

Figure 15:
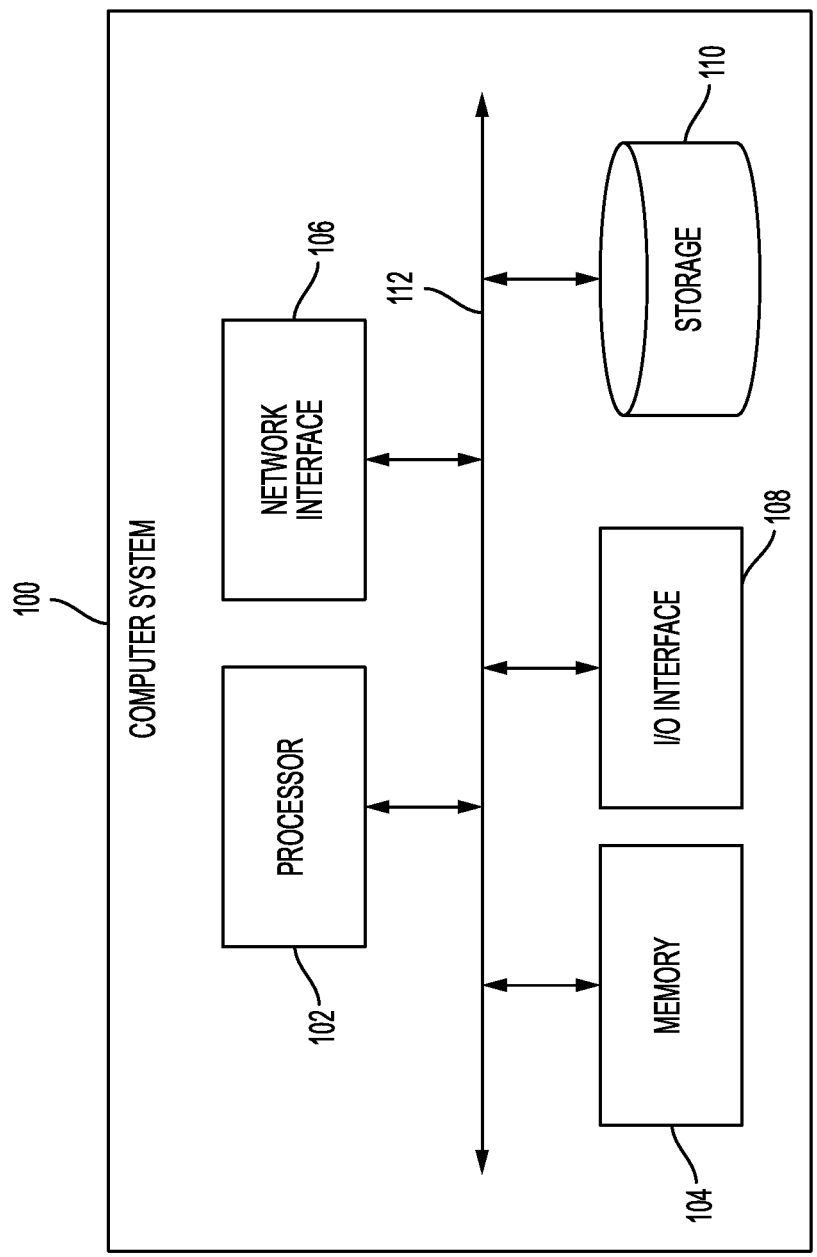
FIG. 15 illustrates one exemplary embodiment of a computer system having one or more features consistent with the present description.

FIG. 15 illustrates one exemplary embodiment of a computer system 100. As shown, the computer system 100 includes one or more processors 102 which can control the operation of the computer system 100. "Processors" are also referred to herein as "controllers." The processor(s) 102 can include any type of microprocessor or central processing unit (CPU), including programmable general-purpose or special-purpose microprocessors and/or any one of a variety of proprietary or commercially available single or multi-processor systems. The computer system 100 can also include one or more memories 104, which can provide temporary storage for code to be executed by the processor(s) 102 or for data acquired from one or more users, storage devices, and/or databases. The memory 104 can include read-only memory (ROM), flash memory, one or more varieties of random access memory (RAM) (e.g., static RAM (SRAM), dynamic RAM (DRAM), or synchronous DRAM (SDRAM)), and/or a combination of memory technologies.

The various elements of the computer system 100 can be coupled to a bus system 112. The illustrated bus system 112 is an abstraction that represents any one or more separate physical busses, communication lines/interfaces, and/or multi-drop or point-to-point connections, connected by appropriate bridges, adapters, and/or controllers. The computer system 100 can also include one or more network interface(s) 106, one or more input/output (TO) interface(s) 108, and one or more storage device(s) 110.

The network interface(s) 106 can enable the computer system 100 to communicate with remote devices, e.g., other computer systems, over a network, and can be, for non-limiting example, remote desktop connection interfaces, Ethernet adapters, and/or other local area network (LAN) adapters. The TO interface(s) 108 can include one or more interface components to connect the computer system 100 with other electronic equipment. For non-limiting example, the TO interface(s) 108 can include high speed data ports, such as universal serial bus (USB) ports, 1394 ports, Wi-Fi, Bluetooth, etc. Additionally, the computer system 100 can be accessible to a human user, and thus the TO interface(s) 108 can include displays, speakers, keyboards, pointing devices, and/or various other video, audio, or alphanumeric interfaces. The storage device(s) 110 can include any conventional medium for storing data in a non-volatile and/or non-transient manner. The storage device(s) 110 can thus hold data and/or instructions in a persistent state, i.e., the value(s) are retained despite interruption of power to the computer system 100. The storage device(s) 110 can include one or more hard disk drives, flash drives, USB drives, optical drives, various media cards, diskettes, compact discs, and/or any combination thereof and can be directly connected to the computer system 100 or remotely connected thereto, such as over a network. In an exemplary embodiment, the storage device(s) can include a tangible or non-transitory computer readable medium configured to store data, e.g., a hard disk drive, a flash drive, a USB drive, an optical drive, a media card, a diskette, a compact disc, etc.

The elements illustrated in FIG. 15 can be some or all of the elements of a single physical machine. In addition, not all of the illustrated elements need to be located on or in the same physical machine. Exemplary computer systems include conventional desktop computers, workstations, minicomputers, laptop computers, tablet computers, personal digital assistants (PDAs), mobile phones, and the like.

The computer system 100 can include a web browser for retrieving web pages or other markup language streams, presenting those pages and/or streams (visually, aurally, or otherwise), executing scripts, controls and other code on those pages/streams, accepting user input with respect to those pages/streams (e.g., for purposes of completing input fields), issuing HyperText Transfer Protocol (HTTP) requests with respect to those pages/streams or otherwise (e.g., for submitting to a server information from the completed input fields), and so forth. The web pages or other markup language can be in HyperText Markup Language (HTML) or other conventional forms, including embedded Extensible Markup Language (XML), scripts, controls, and so forth. The computer system 100 can also include a web server for generating and/or delivering the web pages to client computer systems.

In an exemplary embodiment, the computer system 100 can be provided as a single unit, e.g., as a single server, as a single tower, contained within a single housing, etc. The single unit can be modular such that various aspects thereof can be swapped in and out as needed for, e.g., upgrade, replacement, maintenance, etc., without interrupting functionality of any other aspects of the system. The single unit can thus also be scalable with the ability to be added to as additional modules and/or additional functionality of existing modules are desired and/or improved upon.

A computer system can also include any of a variety of other software and/or hardware components, including by way of non-limiting example, operating systems and database management systems. Although an exemplary computer system is depicted and described herein, it will be appreciated that this is for sake of generality and convenience. In other embodiments, the computer system may differ in architecture and operation from that shown and described here.

The devices disclosed herein can also be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, components of the invention described herein will be processed before use. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high energy electrons. The radiation kills bacteria on the instrument and in the container. The sterilized instrument can then be stored in the sterile container. The sealed container keeps the instrument sterile until it is opened in the medical facility.

Typically, the device is sterilized. This can be done by any number of ways known to those skilled in the art including beta or gamma radiation, ethylene oxide, steam, and a liquid bath (e.g., cold soak). An exemplary embodiment of sterilizing a device including internal circuitry is described in more detail in U.S. Pat. No. 8,114,345 filed Feb. 8, 2008 and entitled "System And Method Of Sterilizing An Implantable Medical Device." It is preferred that device, if implanted, is hermetically sealed. This can be done by any number of ways known to those skilled in the art.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A surgical tool, comprising:
a housing configured to couple to a plurality of motors on a tool driver of a surgical robot;
an elongate shaft extending distally from the housing and having an end effector coupled to a distal end thereof, the elongate shaft having a longitudinal axis extending between a proximal end and the distal end thereof;
a drive assembly disposed within the housing and configured to be driven by a motor on a tool driver of a surgical robot;
an actuator mechanism extending through the elongate shaft and operatively coupled between the drive assembly and the end effector for actuating the end effector, the actuator mechanism having a plurality of drivers and a plurality of end effector actuators, each one of the plurality of end effector actuators being configured to engage a corresponding one of the plurality of drivers, and each of the plurality of drivers being configured to engage and be rotated by the drive assembly for actuating the end effector; and
a bailout mechanism directly coupled to the actuator mechanism and being configured to rotate around the longitudinal axis to apply a proximal force to the actuator mechanism to retract the actuator mechanism, the bailout mechanism being configured to rotate one of the plurality of drivers, which is configured to rotate one of the plurality of end effector actuators to apply a proximal force to retract the actuator mechanism.

2. The surgical tool of claim 1, wherein the bailout mechanism includes a rotatable wheel disposed within the housing and configured to be rotated to apply a proximal force to the actuator mechanism.

3. The surgical tool of claim 2, wherein the bailout mechanism includes a crank arm configured to manually rotate the rotatable wheel.

4. The surgical tool of claim 3, further comprising a pawl coupled to the crank arm and engageable with the rotatable wheel, the pawl being configured to rotate the wheel in a direction that causes retraction of the actuator mechanism.

5. The surgical tool of claim 2, further comprising a pawl engaged with the rotatable wheel and configured to limit rotation of the rotatable wheel in only one direction.

6. The surgical tool of claim 1, wherein the plurality of end effector actuators are configured to engage the plurality of drivers through a groove and tooth engagement.

7. The surgical tool of claim 1, further comprising an alignment feature formed in the housing and configured to mate with a corresponding alignment feature on the tool driver of the surgical robot.

8. The surgical tool of claim 1, wherein the bailout mechanism is recessed on an outermost surface of the housing.

9. A surgical tool, comprising:
an elongate shaft having a longitudinal axis;
an end effector coupled to a distal end of the elongate shaft, the end effector including first and second jaws movable between an open position in which the first and second jaws are spaced apart from one another, and a closed position in which the first and second jaws are configured to engage tissue therebetween;
a plurality of actuation members extending distally through the elongate shaft and configured to operate on the end effector;
a plurality of driving members configured to engage and be rotated by a drive assembly, each driving member coupled to a corresponding actuation member, each driving member being configured to cause forward and reverse actuation of the corresponding actuation member for actuating the end effector; and
a bailout mechanism configured to engage the plurality of driving members, the bailout mechanism configured to be manually rotated around the longitudinal axis to rotate one of the plurality of driving members, which is configured to rotate the corresponding actuation member to cause reverse actuation.

10. The surgical tool of claim 9, wherein the bailout mechanism includes a rotatable wheel.

11. The surgical tool of claim 10, wherein the bailout mechanism includes a crank arm configured to manually rotate the rotatable wheel and a pawl coupled to the crank arm and engageable with the rotatable wheel, the pawl being configured to rotate the wheel in a direction that causes reverse actuation of the corresponding actuation member.

12. The surgical tool of claim 9, further comprising a housing with an alignment feature formed thereon, the alignment feature being configured to mate with a corresponding alignment feature on a tool driver of a surgical robot.

13. The surgical tool of claim 12, wherein the bailout mechanism is recessed on an outermost surface of the housing.

14. The surgical tool of claim 9, wherein, when the bailout mechanism is manually rotated, the bailout mechanism is configured to cause rotation of the corresponding actuation member with respect to the longitudinal axis to reverse operation of the end effector.

* * * * *